United States Patent [19]

Masuda et al.

[11] Patent Number: 4,710,003
[45] Date of Patent: Dec. 1, 1987

[54] CORNEA SHAPE MEASURING APPARATUS

[75] Inventors: Takashi Masuda, Kawasaki; Yukitugu Nakamura, Sagamihara; Kyoji Sekiguchi, Tokyo, all of Japan

[73] Assignee: Canon Kabushiki Kaisha, Tokyo, Japan

[21] Appl. No.: 833,660

[22] Filed: Feb. 21, 1986

Related U.S. Application Data

[63] Continuation of Ser. No. 543,041, Oct. 18, 1983, abandoned.

[30] Foreign Application Priority Data

Oct. 21, 1982 [JP] Japan ................................. 57-185290
Oct. 26, 1982 [JP] Japan ................................. 57-188434

[51] Int. Cl.$^4$ ............................................... A61B 3/10
[52] U.S. Cl. ......................................... 351/212; 351/211
[58] Field of Search ................. 351/205, 211, 212, 208

[56] References Cited

U.S. PATENT DOCUMENTS 4,312,574 1/1982 Wilms ................................. 351/212
4,315,672 2/1982 Muller et al. ....................... 351/212
4,355,871 10/1982 Nenyas et al. ..................... 351/212

Primary Examiner—Rodney B. Bovernick
Assistant Examiner—D. M. Dzierzynski
Attorney, Agent, or Firm—Fitzpatrick, Cella, Harper & Scinto

[57] ABSTRACT

In a cornea shape measuring apparatus wherein a chart for measurement is projected onto the cornea of an eye to be examined and the shape of the corneal reflection image thereof is detected through a measuring optical system to thereby measure the shape of the cornea, there is provided an observation optical system for enabling the corneal reflection image to be always observed. The magnification of the observation optical system is made smaller than the magnification of the measuring optical system and the fore eye portion and the corneal reflection image are always observable.

12 Claims, 13 Drawing Figures 4,710,003

CORNEA SHAPE MEASURING APPARATUS

This application is a continuation of application Ser. No. 543,041 filed Oct. 18, 1983, now abandoned.

BACKGROUND OF THE INVENTION

1. Field of the Invention

This invention relates to an ophthalmologic measuring apparatus, and in particular to a cornea shape measuring apparatus.

2. Description of the Prior Art

A keratometer for measuring cornea shape is usually used to measure the three elements of a cornea, i.e., the curvature, the degree of astigmatism and the direction of astigmatic axis, and in addition, is used to inspect the base curve of contact lenses.

In the conventional keratometer, the shape of the corneal reflection image of a ring-shaped chart has been observed and measured by naked eyes and therefore, the magnification has been set to a high level to obtain satisfactory accuracy, thereby enlarging the corneal reflection image.

As a result, the range which can be observed during alignment and during measurement has been limited to only a part of the cornea and it has been very difficult to grasp what area of the entire cornea is actually being measured There has been a certain type of keratometer in which the optical path can be changed over to enable the fore eye portion to be observed, but in such keratometer, measurement must be effected with the optical path returned to its original position and thus, the aforementioned disadvantage has been unavoidable during measurement.

SUMMARY OF THE INVENTION

In view of the above-noted point, it is an object of the present invention to provide a cornea shape measuring apparatus which enables the fore eye portion and the corneal reflection image to be always observed irrespective of alignment and measurement without the accuracy of measurement being reduced. To achieve such object, the present invention is characterized in that an observation optical system branching off from the measuring optical path or from the measuring light flux is provided and the magnification of the observation optical system is made smaller than the magnification of the measuring optical system to thereby widen the observation field.

It is a further object of the present invention to provide a cornea shape measuring apparatus in which alignment is facilitated.

The invention will become fully apparent from the following detailed description thereof taken in conjunction with the accompanying drawings.

DESCRIPTION OF THE PREFERRED EMBODIMENT

Figure 1:
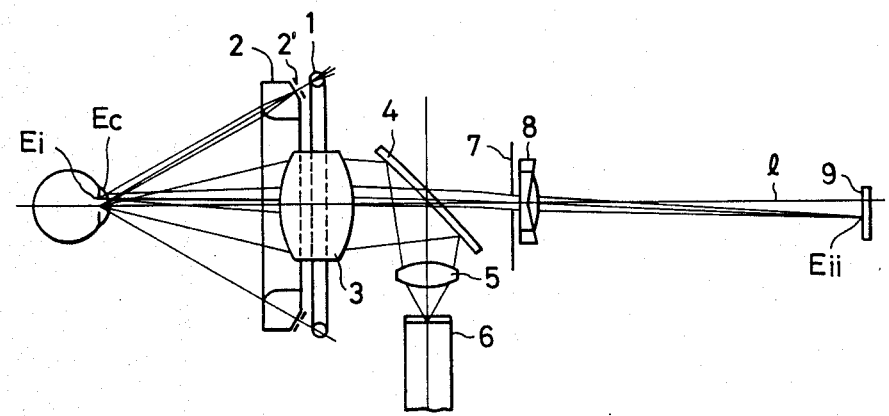
FIG. 1 shows a first embodiment of the present invention.

FIG. 1 shows an embodiment of the present invention applied to an automatic keratometer. The light emitted from a circular ring-shaped light source 1 is caused to emerge parallel in each plane containing the optical axis 1 by a circular ring-shaped cylindrical lens 2.

The surface of the circular ring-shaped cylindrical lens 2 which is opposed to the cornea in each plane containing the optical axis 1 has a radius of curvature r, and the lens 2 has a circular ring-shaped slit 2' at a position spaced apart by the focal length f thereof. The light having emerged from the slit 2' emerges parallel in each plane containing the optical axis 1 and illuminates the cornea Ec of the eye to be examined.

The light reflected by the cornea Ec diverges and apparently emerges from a corneal reflection image position Ei. This corneal reflection image Ei is transmitted through an objective lens 3 and a light-dividing mirror 4, has its optical path divided and deflected by a plural-aperture stop 7 and a deflecting prism 8 and is imaged as Eii on a light-receiving element 9. Such an optical path from the eye to be examined to the light-receiving element 9 is an optical path used for measurement.

Figure 2:
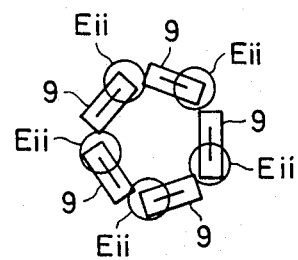
FIG. 2 shows the positional relation between light-receiving elements and a corneal reflection image.

The light-receiving element 9 is, for example, a one-dimensional image sensor and, as shown in FIG. 2, five such light-receiving elements are disposed on a circumference and receive light fluxes deflected into five light fluxes by the plural-aperture stop 7 and the deflecting prism 8. If five points of intersection between the one-dimensional image sensors and the corneal reflection image of the circular ring-shaped slit are found as shown in FIG. 2, the general elliptical shape of the cornea can be found by substituting them into the general equation of quadratic curve $ax^2+by^2+cxy+dx+ey+f=0$ and finding each coefficient, and the curvature, degree of astigmatism and direction of astigmatic axis of the cornea can be calculated therefrom.

What has been described above is the measuring optical system, and the observation optical system according to the present invention will hereinafter be described.

In FIG. 1, the light flux reflected by the light-dividing mirror 4 images the corneal reflection image and the fore eye portion around it on an image pick-up tube 6 by an imaging lens 5. The light-dividing mirror 4 may be a wavelength-dividing mirror which reflects and transmits light in accordance with the spectral sensitivities of the image pick-up tube 6 and the light-receiving elements 9, or alternatively may be a beam splitter having a reflection-transmission ratio matching the relative sensitivities of the image pick-up tube and the light-receiving elements.

The imaging lens 5 is a lens for imaging the corneal reflection image and the fore eye portion at a magnification matching the size of the image pick-up tube. By the use of this lens, the magnification of the observation optical system is set to a magnification smaller than the magnification of the measuring optical system. A variable magnification, variable focus lens can be used as the imaging lens 5, and it is possible to suitably adjust the observation field as by a zoom lens.

The measuring optical system and the observation optical system have the objective lens 3 in common, and the optical paths subsequent to the light-dividing mirror 4 are independent and therefore, the optical constants such as the magnification, F No., etc. of each optical system can be selected as required.

Figure 3:
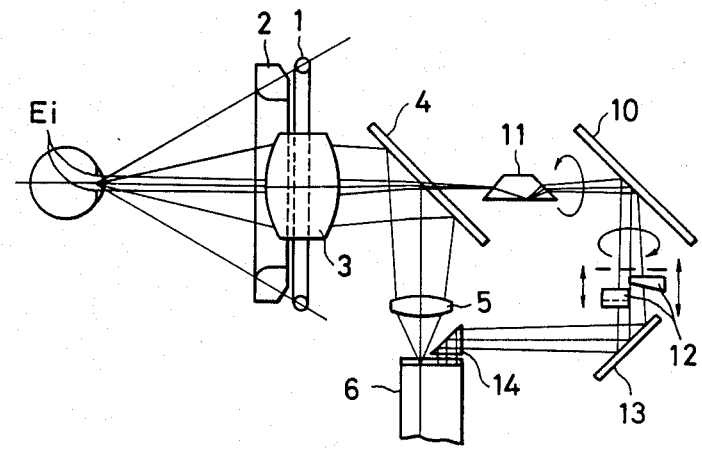
FIG. 3 shows a second embodiment of the present invention.

FIG. 3 shows a second embodiment of the present invention applied to a manually operated keratometer.

In FIG. 3, reference numerals 1 to 6 are similar in significance to those in FIG. 1. The optical path transmitted through the light-dividing mirror 4 is used for measurement and the light flux passed through an image rotator 11 is reflected by a mirror 10, is deflected by a deflecting prism 12, is reflected by a mirror 13 and a reflecting prism 14, reaches the image pick-up tube 6 and images the corneal reflection image.

The deflecting prism 12 is movable in the direction of the optical axis, and the radius of curvature of the cornea is measured from the amount of movement thereof until the divided images become coincident with each other.

The image rotator 11 is rotatable in synchronism with the deflecting prism 12, whereby the angle of astigmatism can be measured.

Figure 4:
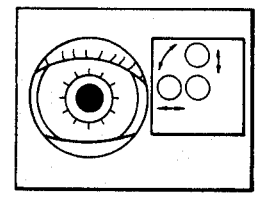
FIG. 4 shows the imaged condition on the image pick-up tube of the second embodiment.

FIG. 4 shows the imaged condition on the image pick-up tube of the FIG. 3 embodiment.

Figure 5:
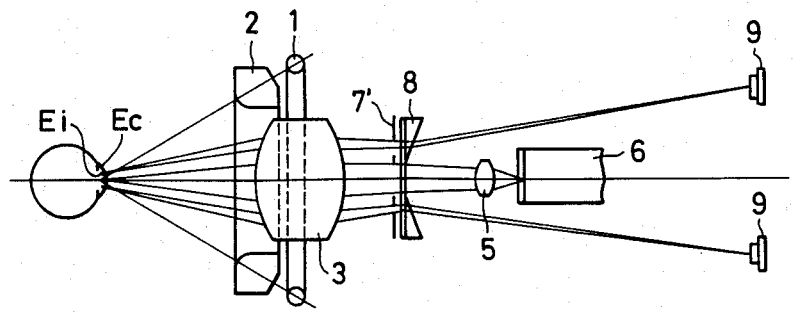
FIG. 5 shows a third embodiment of the present invention.
Figure 6:
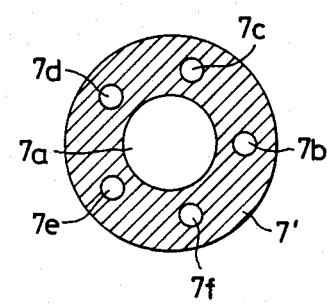
FIG. 6 shows a plural-aperture stop.

FIG. 5 shows a third embodiment of the present invention in which a plural-aperture stop is used as means for separating the measuring optical system and the observation optical system. The plural-aperture stop 7' is shown in FIG. 6. That is, light is directed to the measuring optical system through apertures 7b–7f in the outer peripheral portion of the plural-aperture stop 7' and light is directed to the observation optical system through a central aperture 7a and thus, the light flux is branched off to the two optical systems by the plural-aperture stop 7'.

Figure 7:
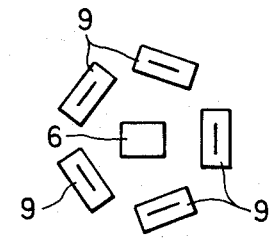
FIG. 7 shows the arrangement of the light-receiving elements and the image pick-up tube.

The relative positional relation between the light-receiving elements 9 and the image pick-up tube 6 as seen from the direction of the optical axis is shown in FIG. 7. Again in this embodiment, the magnification of the observation optical system can be made smaller than the magnification of the measuring optical system to thereby widen the observation field.

Figure 8:
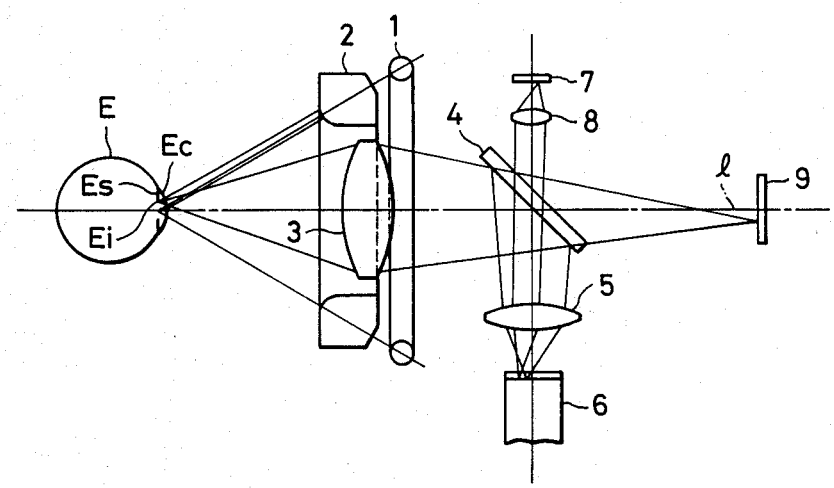
FIG. 8 shows a further embodiment of the present invention.

FIG. 8 shows a further embodiment of the present invention in which alignment is facilitated.

Figure 9:
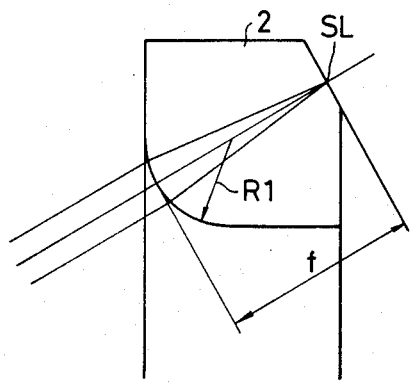
FIG. 9 is a cross-sectional view of a circular ring-like lens.

In FIG. 8, the light emitted from a circular ring-shaped light source 1 (for example, a fluorescent lamp) is caused to emerge parallel in a plane containing the optical axis l by a circular ring-shaped lens 2 and illuminates the cornea Ec of an eye to be examined. The circular ring-shaped lens 2 is a circular ring-shaped cylindrical lens having a refractive power in a plane containing each meridian and the optical axis and having no refractive power in a direction orthogonal thereto and, as shown in FIG. 9, in each plane containing each meridian and the optical axis, it has a circular ring-shaped slit $S_L$ at a position spaced apart from the lens surface of a radius of curvature $R_1$ by the focal length f thereof.

If the cornea is regarded as a reflecting body, the aforementioned light flux appear to be reflected thereby and apparently emerge from the corneal reflection image position Ei.

This corneal reflection image is imaged on the image pick-up tube 6 by the objective lens 3, the light-dividing mirror 4 and the imaging lens 5 and becomes observable. A zoom lens is applicable as the imaging lens 5, and the magnification of the observation optical system can be suitably selected.

The shape of the corneal reflection image changes in conformity with the shape of the cornea Ec of the eye to be examined, and the curvature, refractive index, degree of astigmatism and astigmatic axis of the cornea can be found from that shape.

The measuring system branching off from the observation system is constituted by the light-dividing mirror 4 and light position detector 9.

The light-dividing mirror 4 is a beam splitter such as a half-mirror, or a wavelength dividing mirror and can separate the light flux into light fluxes for the measuring system and the observation system, as required.

By the magnification of the observation optical system being set to a magnification smaller than that of the measuring optical system, the observation field is widened and the corneal reflection image including the fore eye portion becomes observable on the image pick-up tube 6, while in the measuring optical system, the light-dividing mirror 4 and subsequent elements are independent relative to the observation system and therefore, they do not affect the measurement accuracy.

In FIG. 8, reference numeral 7 designates an absolute position index plate provided at a position conjugate with the corneal reflection image. This absolute position index plate 7, with the corneal reflection image and the fore eye portion, is observable on the image pick-up tube 6 through an index mark projection lens 8, the light-dividing mirror 4 and the imaging lens 5.

Figure 10:
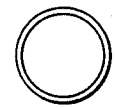
FIG. 10 shows an index mark for alignment.

The absolute position index plate 7 is an index plate for alignment and has a circular ring-shaped opening as shown in FIG. 10, the center of the opening lying on the optical axis of the lens.

The absolute position index mark image is always stationary relative to the image pick-up tube and the examiner can easily accomplish alignment by moving the entire optical system so that the aforementioned corneal reflection image comes to a predetermined position relative to this index mark.

Actually, the positions of the fore eye portion and the corneal reflection image in the direction of the optical axis differ from each other, but if an optical system having a great depth of field is used, the fore eye portion and the corneal reflection image are observable in in-focus state.

Figure 11:
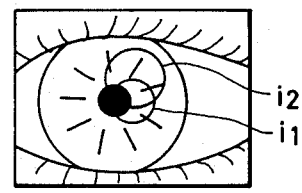
FIGS. 11 to 13 show the imaged conditions on the image pick-up tube, FIG. 11 showing bad alignment and FIGS. 12 and 13 showing good alignment.

FIG. 11 shows the image on the image pick-up tube in a case where in the alignment with the eye to be examined is bad, and in this Figure, $i_1$ designates the image of the absolute position index mark and $i_2$ denotes the corneal reflection image.

Figure 12:
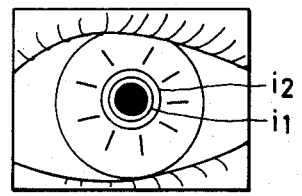
Figure 13:
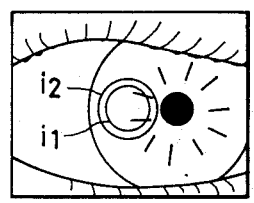

FIGS. 12 and 13 show the image on the image pick-up tube in a case where the alignment with the eye to be examined is good, and these Figures respectively correspond to the cases where the central portion and the marginal portion of the cornea are measured. That is, the corneal reflection image $i_2$ is aligned with the absolute position index mark image $i_1$ as the reference.

According to the present invention, as described above, the fore eye portion and the corneal reflection image are observable irrespective of the alignment or the measurement going on, and the measured region of the eye to be examined can be accurately grasped and also, the state of the eye being measured can be observed and it becomes easy for the examiner to judge the reliability of the measurement data while, at the same time, the absolute position index mark is made observable by enlargement of the observation field, whereby alignment can be accomplished easily.

What we claim is:

1. A cornea shape measuring apparatus comprising:
   a continuous ring-shaped chart for measurement;
   a continuous ring-shaped projecting means having a central axis and a continuous cylindrical surface, formed around the central axis, having a refractive power in each meridian direction but lacking a refractive power in a direction perpendicular thereto for projecting without distortion said chart onto the cornea of an eye to be examined by converting rays emitted from said chart into parallel rays along a direction inclined relative to the central axis in a plane containing the central axis;
   measuring means for measuring the corneal reflection image of said chart;
   a measuring optical system for projecting the corneal reflection image of said chart onto said measuring means;
   observation means for observing the corneal reflection image of said chart; and
   an observation optical system for projecting the corneal reflection image of said chart onto said observation means, the magnification of said observation optical system being less than the magnification of said measuring optical system, such that the area of said eye observable by said observation means is larger than the image area of the corneal reflection image of said chart measured by said measuring means.

2. A cornea shape measuring apparatus according to claim 1, wherein said observation optical system has a variable focus lens.

3. A cornea shape measuring apparatus according to claim 1, wherein said measuring optical system and said observation optical system use at least some of optical members in common.

4. A cornea shape measuring apparatus according to claim 3, wherein said optical member used in common is a wavelength-dividing mirror.

5. A cornea shape measuring apparatus according to claim 3, wherein said optical member used in common is a beam splitter.

6. A cornea shape measuring apparatus according to claim 1, wherein each of the optical paths of said measuring optical system and said observation optical system is an optical path provided by the corneal reflection image light being divided into light fluxes.

7. A cornea shape measuring apparatus according to claim 1, wherein said projecting means comprises a circular ring-shaped cylindrical lens and said chart for measurement is disposed at a focal point position of said cylindrical lens.

8. A cornea shape measuring apparatus according to claim 1, wherein said measuring means measures positional coordinates of five points on the corneal reflection image of said chart for measurement.

9. A cornea shape measuring apparatus according to claim 1, further comprising:
   a chart for alignment provided at a position conjugate with the corneal reflection image of said chart for measurement; and
   a projecting optical system for projecting said chart for alignment onto said observations means.

10. A cornea shape measuring apparatus according to claim 9, wherein said observation optical system has a variable focus lens.

11. A cornea shape measuring apparatus according to claim 9, wherein said projecting means comprises a circular ring-shaped cylindrical lens and said chart for measurement is disposed at a focal point position of said cylindrical lens.

12. A cornea shape measuring apparatus according to claim 9, wherein said measuring means measures positional coordinates of five points on the corneal reflection image of said chart for measurement.

* * * * *